(12) United States Patent
Soudant et al.

(10) Patent No.: US 9,949,918 B2
(45) Date of Patent: Apr. 24, 2018

(54) JOJOBA EXTRACT USEFUL IN IMPROVING SKIN BARRIER FUNCTIONS

(71) Applicant: IBR—ISRAELI BIOTECHNOLOGY RESEARCH LTD., Rehovot (IL)

(72) Inventors: Etienne Soudant, Paris (FR); Ilana Kachko-Chernetsky, Rehovot (IL); Fabien Havas, Rehovot (IL); Olga Ben-Chitrit, Ashdod (IL); Lea Von Oppen-Bezalel, Berlin (DE); Inon Perry, Tel Aviv (IL); Alex Aliluiko, Rehovot (IL)

(73) Assignee: IBR—Israeli Biotechnology Research Ltd., Rehovot (IL)

( * ) Notice: Subject to any disclaimer, the term of this patent is extended or adjusted under 35 U.S.C. 154(b) by 492 days.

(21) Appl. No.: 14/361,701

(22) PCT Filed: Nov. 28, 2012

(86) PCT No.: PCT/IL2012/050484
§ 371 (c)(1),
(2) Date: May 29, 2014

(87) PCT Pub. No.: WO2013/080205
PCT Pub. Date: Jun. 6, 2013

(65) Prior Publication Data
US 2014/0308372 A1    Oct. 16, 2014

Related U.S. Application Data

(60) Provisional application No. 61/564,886, filed on Nov. 30, 2011.

(51) Int. Cl.
| | |
|---|---|
| *A61K 36/185* | (2006.01) |
| *A61K 8/97* | (2017.01) |
| *A61Q 17/00* | (2006.01) |
| *A61Q 19/08* | (2006.01) |
| *A61Q 19/00* | (2006.01) |

(52) U.S. Cl.
CPC .............. *A61K 8/97* (2013.01); *A61K 36/185* (2013.01); *A61Q 17/00* (2013.01); *A61Q 19/08* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 6,890,566 B2 | 5/2005 | Arquette | |
| 7,025,957 B2 | 4/2006 | Arquette | |
| 7,029,709 B2 | 4/2006 | Arquette | |
| 7,097,866 B2 | 8/2006 | Arquette | |
| 7,155,273 B2 * | 12/2006 | Taylor | A61B 5/0059 600/473 |
| 8,101,214 B2 | 1/2012 | Park | |
| 8,168,197 B2 | 5/2012 | Kim | |
| 2003/0008022 A1 | 1/2003 | Mogy | |
| 2004/0156818 A1 | 8/2004 | Lu | |
| 2004/0170712 A1 | 9/2004 | Sadek El Mogy | |
| 2004/0265249 A1 * | 12/2004 | Arquette | A61K 8/602 424/59 |
| 2010/0068310 A1 | 3/2010 | Kim | |
| 2011/0014149 A1 | 1/2011 | Park | |

FOREIGN PATENT DOCUMENTS

| | | |
|---|---|---|
| JP | 2003-034644 | 2/2003 |
| JP | 2003-277261 | 10/2003 |
| WO | 2008/121355 | 10/2008 |
| WO | 2008/148694 | 12/2008 |
| WO | 2009/106934 | 9/2009 |

OTHER PUBLICATIONS

Dreher et al., (1998) Colorimetric method for quantifying human Stratum corneum removed by adhesive-tape stripping. Acta Derm Venereol 78(3): 186-9.

* cited by examiner

*Primary Examiner* — Chris R Tate
*Assistant Examiner* — Randall Winston
(74) *Attorney, Agent, or Firm* — Rodney J. Fuller; Booth Udall Fuller, PLC

(57) ABSTRACT

The present invention provides compositions comprising extracts of Jojoba (*Simmondsia chinensis*) in a polar solvent that are effective in promoting the barrier functions of the skin, useful for improving skin integrity, health and appearance and as anti-aging agent.

21 Claims, 3 Drawing Sheets

JOJOBA EXTRACT USEFUL IN IMPROVING SKIN BARRIER FUNCTIONS

RELATED APPLICATION DATA

This application is the U.S. National Stage of International Application No. PCT/IL2012/050484 filed Nov. 28, 2012, which claims the benefit of United States Provisional Patent Application No. 61/564,886 filed Nov. 30, 2011. Each of the foregoing applications is hereby incorporated by reference in its entirety for all purposes.

FIELD OF THE INVENTION

The present invention relates to the field of skin care, particularly to extracts of Jojoba (*Simmondsia chinensis*) that are effective in promoting the barrier functions of the skin, useful for improving skin integrity, structure and strength and as skin anti-aging agent.

BACKGROUND OF THE INVENTION

The skin serves numerous functions but its primary function is as a protective layer or barrier. The most important role of the skin for terrestrial animals is to protect the water-rich internal organs from the dry external environment. In addition, the skin protects internal tissues from harmful chemical and physical forces as well as from the penetration of pathogens.

Skin is a structurally complex thick membrane. The skin is composed of the epidermis, the dermis, the hypodermis, and the adenexal structures (epidermal appendages). The epidermis, the outermost epithelial tissue of the skin, is itself composed of several layers—the stratum corneum, the stratum granulosum, the stratum spinosum, and the stratum basale. The epidermis is mainly constructed of keratinocytes, and is in a constant state of self-replacement. At the bottom layer, keratinocyte stem cells divide into daughter cells that are displaced outward, and which differentiate through successive overlying layers to enter the stratum corneum. Then, the keratinocyte cells go through apoptosis and die, and their cellular organella and cytoplasm disappear during the final process of differentiation.

The water impermeability function of the skin resides in the upper thinnest layer (approximately 10-20μ in humans) of stratum corneum (SC), having about three magnitudes of order higher water resistance compared to other membranes of living organisms.

The hydration state of the stratum corneum is important for its barrier function as well as for the healthy and firm appearance of the skin. Stratum corneum hydration and transepidermal water loss (TEWL) are two key indexes used for its characterization, typically showing an inverse relationship. High TEWL values, as a marker of disturbed skin barrier function, are frequently correlated with low hydration of the Stratum corneum. Disrupted barrier functions can result inter alia, from skin cleansing with soaps and detergents or from various diseases of the skin. For example, in atopic dermatitis skin barrier disruption has been confirmed by electron microscopy and penetration studies, and lesional atopic dermatitis show high TEWL values. The mechanisms of this interplay of the stratum corneum hydration and transepidermal water loss have not been studied exhaustively. It is suggested however, that disturbed skin barrier function leads to changes in epidermal differentiation.

Tissue integrity is highly dependent on proper cell to cell adhesion, performed by Cell-to-Cell Junctions. Cell-To-Cell Junctions are complexes comprising transmembrane adhesive proteins, and their forms and distribution may vary according to the tissue type. In the skin the prominent junctions are desmosomes, tight and gap junctions.

Desmosomes are intercellular junctions that tightly link adjacent cells. The protein desmoplakin is an obligatory component of functional desmosomes, which anchors intermediate filaments to desmosomal plaques.

Tight junctions (TJ) are cell-cell junctions which connect neighboring cells, control the paracellular pathway of molecules ("barrier function") and separate the apical part from the basolateral part of a cell membrane ("fence function"). The composition of the tight junctions seems to be very important for their barrier function in the epidermis. Down-regulation as well as overexpression of certain proteins perturbs this barrier. Damage to the tight junctions is linked to skin water loss, dry and sensitive skin and to several skin disorders, including psoriasis vulgaris, lichen planus, cholangitis and ichthyosis, including ichthyosis vulgaris.

Gap Junctions are organized collections of protein channels in cell membranes that allow ions and small molecules to pass between adjacent cells. The protein channels that make up gap junctions consist of two hexagonal arrays of membrane-spanning proteins termed connexons. One connexon resides in the membrane of one cell. It aligns and joins the connexon of the neighboring cell, forming a continuous aqueous pathway by which ions and small molecules can freely (passively) pass from one cell to the other.

Several synthetic compounds as well as plant extracts have been shown to affect the skin barrier function. For example, U.S. Pat. No. 8,101,214 discloses herbal extract complex of several Chinese herbs at a ratio of the plant extracts that is superior in promoting the differentiation of skin keratinocytes, restoring impaired skin barrier function and increasing skin moisturization as compared to extracts obtained by extracting each of the herbs alone.

U.S. Pat. No. 8,168,197 discloses a skin external composition for alleviating dry skin symptoms, which contains an extract of *Scrophularia buergeriana* Miq. as a main component and further contains an extract of *Poria cocos* Wolf, as well as the use thereof for skin-moisturizing cosmetics. The composition contains, as active ingredients, the *Scrophularia buergeriana* Miq. extract and the *Poria cocos* Wolf extract, which are prepared by extracting each separately, using water, ethanol, methanol, hexane, ethyl acetate or butanol.

U.S. Patent Application Publication No. 20040156818 discloses compositions comprising a blend of neem seed cell broth and one or more additional botanical ingredients or pomegranate fruit extract and, optionally, one or more additional botanical ingredients which are useful, among others, in reduction in skin fragility, improvement in skin barrier repair and/or function and improvement in skin moisturization.

International (PCT) Patent Application Publication No. WO 2008/148694 discloses a moisturizing cosmetic composition comprising a galacto-oligosaccharide that consists of 4 to 10 monosaccharide units and has at least one fructose residue. This galacto-oligosaccharide may be obtained from a plant belonging to the Lamiaceae family flora. An extract from this plant showed improved skin moisturizing effect without stickiness, and a synergetic moisturizing effect with polyhydric alcohols.

International (PCT) Patent Application Publication No. WO 2009/106934 discloses Angico-Branco (*Piptadenia colubrina*) extract useful as a skin barrier protective and moisturizing agent, due to mechanisms involving stimulation of the expression of aquaporin-3, fibronectin and the envelope proteins filaggrin and involucrin. The invention further relates to cosmetics and dermatological formulations comprising the extract for facial or body treatment of specific skin changes such as skin dryness, cracking, scaling, flaking or any disturbance involving skin barrier disruptions.

Exemplary list of plant extract based products useful in promoting skin barrier function, already available on the market include PhytoCellTec Alp Rose of Mibelle Industries, Switzerland and Phytoglycolipid II of Barnet Products, U.S.A.

The continuously growing list of products and technologies attempting to improve the skin barrier functions show that a universally useful solution is not yet available.

Jojoba (*Simmondsia chinensis*) is a shrub native to the Sonoran and Mojave deserts of Arizona, California, and Mexico. It is the sole species of the family Simmondsiaceae, placed in the order Caryophyllales. It is also known as goat nut, deer nut, pignut, wild hazel, quinine nut, coffeeberry, and gray box bush. Jojoba is grown commercially for its oil, a liquid wax ester present in the seeds. Jojoba oil is used as a replacement for whale oil and its derivatives, such as cetyl alcohol. Prohibiting the import of whale oil to the U.S. in 1971 led to the discovery that jojoba oil is in many regards superior for applications in the cosmetics and other industries. Jojoba oil is also a fungicide, and can be used for controlling mildew. Like olestra, jojoba oil is edible but non-caloric and non-digestible. Jojoba biodiesel has been explored as a cheap, sustainable fuel that can serve as a substitute for petroleum diesel.

Use of hydrophilic extracts of Jojoba has been previously disclosed only for whitening and exfoliating skin, utilizing the jojoba meal, particularly the meal retained after the oil extraction. The meal is mainly used as a mechanical peal in combination of one or more hydroxy acids (U.S. Pat. Nos. 6,890,566, 7,025,957, 7,029,709, 7,097,866).

As described hereinabove, promotion of barrier function and subsequent maintenance of skin integrity are important for improving skin appearance and health including treating and/or alleviating various skin disorders. It is highly desirable and it would be advantageous to have compositions and methods effective in promoting the barrier functions of the skin, particularly plant-derived compositions known not to have deleterious effects.

SUMMARY OF THE INVENTION

The present invention relates to Jojoba plant extracts, particularly to extracts of the aerial part of the plant that are useful in improving skin structure, strength and cohesion and in promoting the barrier functions of the skin.

The present invention is based in part on the unexpected discovery that extracting the leaves parts of Jojoba in a polar solvent, particularly water, results in an extract effective in the maintenance and/or promotion of the skin barrier function. Particularly, the extracts of the present invention significantly enhanced the expression of the desmoplakin I, desmoplakin II and cytokeratin 5 encoding genes as well as several other keratin encoding genes. Without wishing to be bound by any specific theory or mechanism of action, the promotion of skin integrity may thus be due to the presence of desmoplakin, an obligatory component of functional desmosomes and of several types of keratin, including cytokeratin 5, cytokeratin 2A and cytokeratin 1, known to be essential for the proper differentiation of simple and stratified epithelial tissues. The extracts of the present invention can thus be used to maintain skin integrity and preserve and/or promote the skin barrier function.

Thus, according to one aspect, the present invention provides a method for maintaining and/or promoting the skin structure, strength, cohesion or any combination thereof comprising administering to the skin of a subject a composition comprising as an active ingredient an extract of Jojoba (*Simmondsia chinensis*) plant or any part thereof in a polar solvent, thereby maintaining or promoting the skin barrier function.

According to certain embodiments, the composition comprises the Jojoba extract as the sole active ingredient. According to other embodiments the composition further comprises at least one additional active agent.

According to certain embodiments, maintaining or promoting the skin barrier function comprises at least one of maintaining or reducing the skin dehydration rate, maintaining or promoting the skin hydration value, maintaining or promoting protection from environmental hazards and any combination thereof.

According to other embodiments, the method of the present invention is effective in at least one of improving the skin health, skin integrity skin firmness, skin extensibility, skin elasticity, beautification of overall skin appearance and any combination thereof. Each possibility represents a separate embodiment of the present invention.

According to certain embodiments, improving the skin health includes, but is not limited to, relieving the symptoms of eczema and/or dermatoses, particularly psoriasis vulgaris, lichen planus, cholangitis and ichthyosis, including ichthyosis vulgaris, ichthyosis; prevention of blistering disorders (e.g. Pemphigus Vulgaris); maintaining normal skin homeostasis; facilitating skin wound healing; and any combination thereof. Each possibility represents a separate embodiment of the present invention.

Skin hydration/dehydration value can be measured by any method as is known to a person skilled in the art. According to some embodiments, the predetermined threshold is the value measured before administering the extract of the present invention. According to other embodiments, the predetermined threshold is an average value obtained from individuals with healthy skin. According to yet further embodiments, the predetermined threshold is an average value obtained from individuals with disturbed skin.

The skin parameters can be measured by any method as is known to a person skilled in the art. Common methods for determining the status of the skin barrier function includes examining the skin dehydration by measuring transepidermal water loss (TEWL) value and/or examining the skin hydration by measuring the moisturizing index of the skin (% or arbitrary units).

According to certain embodiments, the polar solvent extracting the Jojoba plant or parts thereof is selected from the group consisting of water, ethanol, propylene glycol, butylene glycol, methanol, glycerol, propanol, butanol, dipropylene glycol, pentylene glycol, hexylene glycol, dimethyl formamide, acetonitrile, dimethyl sulfoxide, dichloromethane, ethyl acetate, tetrahydrofuran, formic acid, acetic acid and acetone or any combination thereof. Each possibility represents a separate embodiment of the present invention.

According to certain typical embodiments, the polar solvent is water. According to other embodiments, the extract is obtained with water and at least one additional polar solvent. According to certain embodiments, the extraction medium comprises water at 30-90% and a polar solvent at 10-70%.

According to certain embodiments, the extract is obtained from any one of the raw Jojoba plant parts, including roots, stems, leaves, seeds, fruit and any combination thereof. According to some embodiments, the extract is obtained from the aerial parts of the Jojoba plant. According to currently typical embodiments, the extract is obtained from leaves and stems. According to certain embodiments, the leaves are green to brown in color. According to other embodiments, stems are of a diameter of from 1-5 mm, typically around 2 mm. The Jojoba plant being dioecious, plant parts may be taken from a female as well as from a male plant and at any time of development.

According to certain embodiments, fresh Jojoba plant parts are taken for extraction. According to other embodiments, the plant parts are partially or completely dried before extraction.

According to certain embodiments, the plants or the parts thereof are added to the extraction solvent as picked. According to other embodiments, the plants or the parts thereof are cut to pieces before the solvent is added. According to yet additional embodiments, the plant or the parts thereof are ground before the solvent is added.

It is to be explicitly understood that the Jojoba plant material, apart from the option of being dried or cut, is not subject to any processing before being extracted according to the teachings of the present invention. Accordingly, the Jojoba plant parts used according to the teachings of the present invention are referred to as "raw plant material" as defined hereinbelow.

According to certain embodiments, the composition comprises the Jojoba extract at a concentration of from 0.003% to 30%, weight to weight (w/w) in respect to the total weight of the composition. According to some embodiments, the Jojoba extract is in the range of 0.3% to 10%. According to typical embodiments, the concentration of the Jojoba extract within the composition is from 1% to 3% (w/w) in respect to the total weight of the composition.

According to certain embodiments, the composition is a cosmetic or pharmaceutical composition, further comprising a cosmetically or pharmaceutically acceptable diluent, carrier or excipient.

According to some embodiments, the cosmetic or pharmaceutical composition further comprises additives useful in the cosmetic and/or dermatological fields, including, but not limited to, fats, emulsifiers and co-emulsifiers, hydrophilic or lipophilic gelling agents, preservatives, solvents, fragrances, fillers, hydrophilic and lipophilic filters, dyestuffs, neutralizers, penetration-enhancing agents and polymers. The quantities of these various additives are those conventionally used in cosmetic and dermatological preparations as is known to a person skilled in the art. Each possibility represents a separate embodiment of the present invention.

According to certain typical embodiments, the at least one additive is selected from the group consisting of, but not limited to, ascorbic acid, its derivatives and corresponding salts, glycerin, citric acid, acetic acid, sulfites, phenoxyethanol, EDTA, diethylmalate, t-Butyl-hydroquinone, aminoguanidine, nicotinic acid/Niacin, nicotinamide, stannous chloride, glucose oxidase, polyvinylpolypyrrolidone, phosphoric acid and cosmetically/pharmaceutically acceptable base. Each possibility represents a separate embodiment of the present invention.

According to additional embodiments, the cosmetic or pharmaceutical composition further comprises at least one additional plant extract and/or microalgae extract.

According to certain currently typical embodiments, the composition comprises a water extract of Jojoba and at least one additional active ingredient selected from the group consisting of agents having short term or long term moisturizing effect, including, but not limited to hyaluronate; radical scavenger and/or anti-oxidant, including, but not limited to tocopherols, Co-Q 10, ascorbic acid and derivatives thereof and carotenoids; UV filters, including, but not limited avobenzone (Butyl Methoxydibenzoylmethane), titanium dioxide, zinc oxide and carotenoids; and anti wrinkling agents, including, but not limited to *Leucojum aestivum* extract.

According to certain embodiments, the composition is for topical administration. Any topical formulation may be used as is known in the art, as long the formulation preserves the extract activity. According to certain embodiments, the composition is administered in a form selected from the group consisting of aqueous solution, cream, lotion, emulsion including water in oil or oil in water emulsion, microemulsion or nanoemulsion, gel, serum and milk.

According to additional embodiments, the composition comprises Jojoba extract produced by a method comprising the steps of:

(a) mixing a Jojoba plant or any part thereof with at least one polar solvent;

(b) incubating the mixture for a time period sufficient to form a liquid extract;

(c) removing the Jojoba plant or part thereof and collecting the liquid extract;

(d) filtering the liquid extract; and (e) collecting the filtrate.

According to certain embodiments, incubating the mixture comprises incubation for a period of from 10 min to 24 h, typically from 40 min to 12 h, more typically from 40 min to 2 h.

According to additional embodiments, the incubation temperature is in the range of 20-120° C., typically of 60-120° C., more typically 80-110° C.

According to certain embodiments, step (c) comprises centrifugation for removing the Jojoba plant parts. According to other embodiment, step (d) comprises filtering the liquid extract through a sieve. According to yet additional embodiments, the method further comprises filtering the filtrate of step (e) through a filter having a pore size of less than 1.5 μm.

Other objects, features and advantages of the present invention will become clear from the following description and drawings.

BRIEF DESCRIPTION OF THE DRAWINGS

FIG. 2 shows the RNA quality and quantity control in keratinocytes after 24 h of treatment with the Jojoba extract.

DETAILED DESCRIPTION OF THE INVENTION

Figure 1:
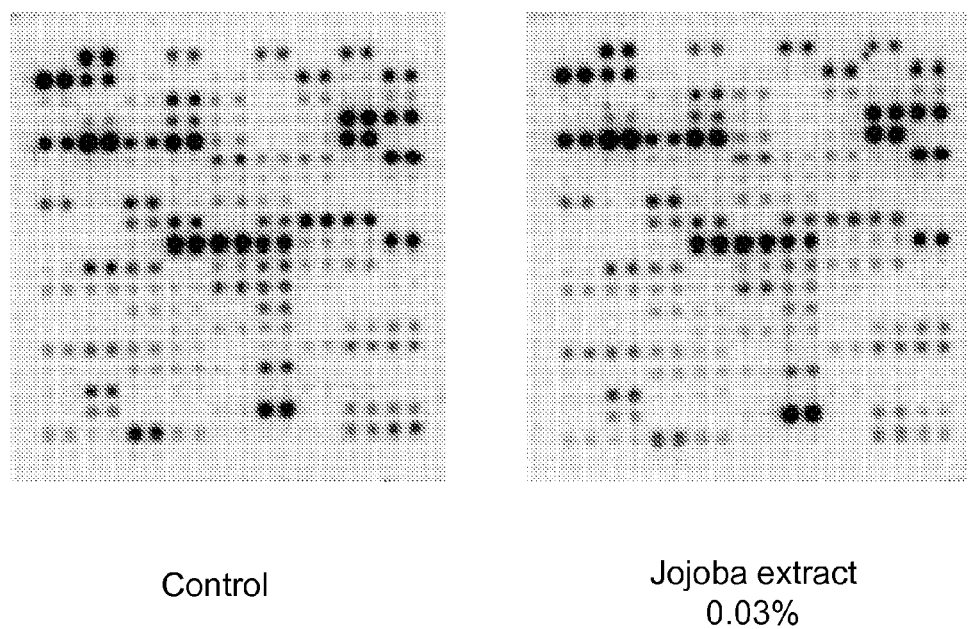
FIG. 1 shows the expression of the examined genes in control (FIG. 1A) and treated (FIG. 1B) keratinocyte. The gene pattern on the membrane is as presented in Table 1.

The present invention discloses extracts of the Jojoba plant useful in improving skin structure, strength and cohesion and thereby promoting the barrier functions of the skin. The extracts of the invention are produced from parts of the plant immersed in at least one polar solvent, particularly in water.

Unexpectedly, the present invention now shows that aqueous and/or additional polar solvent extracts of Jojoba are highly effective in maintaining and/or promoting the skin structure and barrier functions. Without wishing to be bound by any specific theory or mechanism of action, this improvement may be due to the activation of key components in the skin management system. Particularly, the extracts of the present invention significantly enhanced the expression of principal genes involved in the mechanism of proper barrier function, including, inter alia, the genes encoding desmoplakin I & II, syndecan 1, involucrin and fibronectin, and genes involved in keratinocyte differentiation, including the genes encoding cytokeratin 5, cytokeratin 2E/A and cytokeratin 1 and cytokeratin 10.

A significant advantage of the extract of the present invention is thus its ability to activate intrinsic mechanisms of the skin tissue contributing to proper skin structure and barrier functions. Maintaining and/or promoting the skin structure and barrier functions influence a large number of parameters having positive effects on skin health and juvenile appearance.

Thus, according to one aspect, the present invention provides a method for maintaining and/or promoting the skin barrier function comprising administering to the skin a composition comprising an extract of Jojoba or any part thereof in a polar solvent, thereby maintaining or promoting the skin barrier functions.

As used herein, the terms "raw Jojoba plant material" or "raw plant material" refer to any part of the Jojoba plant, either fresh or dry, which is taken for extraction with at least one polar solvent. Optionally, the raw material is cut to pieces, shredded or ground before it is added to the solvent. It is to be explicitly understood that the term does not include Jojoba plant material that was subjected to any one of supercritical $CO_2$ (SCCO2) extraction, hydrolysis, oil fraction removal or any combination thereof prior to extraction with the at least one polar solvent.

According to certain embodiments of the present invention, the raw plant material includes aerial parts of the jojoba plant.

As used herein, the term "aerial parts" when referring to Jojoba plants refers to all plant parts that are above ground, including stems, leaves, flowers, seeds, fruit, buds etc. According to certain currently typical embodiments, the extracts of the present invention are prepared form Jojoba stems and/or leaves. According to certain embodiments, the plant raw plant material does not include seeds.

Jojoba is a dioecious type of plant, i.e. male organs and female organs are located on different plants. The extracts of the present invention can be produced from all type of plants, and plant parts can be taken for extraction at any developmental stage.

According to certain embodiments, the extract of the present invention is produced from Jojoba female plant or parts thereof. According to other embodiments, the extract of the present invention is produced from Jojoba male plant or parts thereof. According to certain typical embodiments, the extract is produced from a combination of female and male plants or parts thereof.

According to certain embodiments, fresh Jojoba plant parts are taken for extraction. According to other embodiments, the plant parts a partially or completely dried before extraction.

Any method as is known to a person skilled in the art can be used to dry the plant material before extraction. For example, the plant material can be oven-dried, sun dried, or dried in the dark under ambient conditions. As used herein, the term "partially dried" refers to plant material comprising about 5% to 80% of the initial water content. Typically, partially dried material contains about 10% of water or less. The term "completely dried" when used in regard to plant material refers to the state where no further weight loss can be detected upon further incubation under the drying conditions.

Regardless of the drying state, the parts of the Jojoba plants can be taken for extraction as a whole, cut to pieces of various sizes or ground to powder before being placed in the extracting solvent.

The plant or its parts is then placed in a polar solvent. The term "polar solvent" as used herein refers to a solvent having a dielectric constant of about 5 or greater. According to certain embodiments, the extract of the present invention is prepared with water as the solvent. According to other embodiments, the solvent used for extraction is selected from the group consisting of, but not limited to, ethanol, propylene glycol, butylene glycol, methanol, glycerol, propanol, butanol, dipropylene glycol, pentylene glycol, hexylene glycol, dimethyl formamide, acetonitrile, dimethyl sulfoxide, dichloromethane, ethyl acetate, tetrahydrofuran, formic acid, acetic acid and acetone. Each possibility represents a separate embodiment of the invention. According to yet additional embodiments, the extraction is performed with a combination of at least two polar solvents. According to certain embodiments, extraction is performed with water and at least one additional polar solvent.

Incubation time of the plant parts within the polar solvent(s) can be varied, depending on the plant parts used, their size and drying state. According to certain embodiments, the incubation time ranges from 10 min to 24 h.

Extractions of the polar substances from the Jojoba plant material into the solvent may be optionally enhanced by heating, applying ultra-sound wave, microwave and other methods as are known in the art. It is to be explicitly understood that although extracting the polar substances using polar solvent(s) is the method currently used to produce the extracts of the present invention, polar substances extracted by any other method as is known in the art, for example cold press of the plant parts, are also encompassed within the scope of the present invention.

Variables related to skin barrier functions in mammals include transepidermal water loss, stratum corneum moisture, skin surface pH, and skin temperature.

Water is of central importance for the function of the skin, and the proportion of water in the skin uppermost layer affects its appearance significantly. In addition to maintaining all transport and other physiological functions in the living layers of the epidermis, water is also of great importance in the horny layer (stratum corneum). Enzymes present in the stratum corneum can adequately exert their activities only at a certain degree of hydration and pH values. Insufficient water content and enzyme activity results in dry, scaly appearance of the skin, which becomes fragile and sensitive and has a tendency toward itching. Altogether, the skin appearance is poor, having fine lines and wrinkles Maintaining the skin water content and preventing dry skin may be primarily achieved by keeping the integrity of the skin tissue and/or its restoration ability, as to reduce damages caused by external aggression to the skin's protective barrier leading to further damage to the skin's intracellular molecules and connective tissues and further water loss through the skin.

Any method for assessing the skin barrier function as is known in the art can be used according to the teachings of the present invention. Techniques to characterize the skin's barrier function include a number of noninvasive methods to measure moisture content and loss through the skin surface. One of these measurements is the determination of skin hydration (HYDR) using a method known as corneometry. This technique determines the capacitance of the skin due to its behavior as a dielectric medium and assesses a 10-20-µm thickness of the stratum corneum. Although it is a measure of the water content of the skin, it is only an indirect measure of barrier function. Nonetheless, it can be related to the extent of HYDR under various physiologic conditions in response to injury, metabolic phenomena, or topical therapies. Values reported for human skin evaluations differ depending on the body site that is studied. Nonetheless, changes in individual or mean HYDR scores in a group of human subjects may serve as an index of skin health, with higher values typically considered more desirable.

Another method is assessment of the integrity of the skin barrier to insensible water loss. This technique is performed by measuring transepidermal water loss (TEWL) through the epidermal surface. The TEWL value is a measure of the rate of water lost through the skin (in $g/h \cdot m^2$) and is an estimate of the skin's ability to retain moisture. The method is based on the measure of water vapor density gradient established in a layer of 10 mm above the skin surface. It is an index of the extent of possible damage of the skin's water-barrier function. Because water loss through the skin normally occurs by passive diffusion through the epidermis, higher TEWL values indicate greater water loss and are consistent with increased damage of the barrier function of the stratum corneum such as may occur during irritant exposure or atopic dermatitis.

As exemplified hereinbelow, the present invention now shows that applying the composition comprising Jojoba extract of the present invention to the skin of the forearm results in significant reduction in the TEWL value. It is thus clearly demonstrated that the composition of the invention is effective in promoting the skin barrier function.

The effect of the compositions of the present invention on the skin structure, strength and barrier function can be further determined by examining the biomechanical properties of the skin. Rheological evaluation is the currently preferred method known to those skilled in the art for non-invasive in vivo measurement of variations induced by the topical application of active agents. Skin has two rheological characteristics: a visco-elastic property with high elasticity and a natural tension which varies depending on the zone. The network formed by tension lines in the skin is called the Langer network. The rheological properties of conjunctive tissue stem from its structure which is basically, a three dimensional network of collagen and elastin fibers. The method enables evaluation of variations in the biological extensibility and elasticity of superficial cutaneous layers, and is typically performed using a Cutometer. In principle, the skin is sucked into the orifice of a probe by constant vacuum pressure for a set length of time. The depth to which the skin penetrates into the probe is measured by two optical prisms located at the opening of the probe's orifice to eliminate the effects of friction and mechanical strain. Based on the results obtained the following biomechanical parameters can be analyzed: tension, firmness, tone (if the residual elongation decreases, skin is more tonic), and suppleness (if the immediate elongation increases, skin is suppler).

The skin strength, particularly the strength and barrier function of the stratum corneum can be further evaluated suing the tap stripping protocol. According to the principles of this assay, a patch is quickly (in a range of seconds) applied onto a volunteer. Then, the patch is slowly removed and analyzed to quantify the amount of removed SC. The analyses can be by the removed SC weight, protein amount and/or visual imaging (Dreher, F et al., 1998. Acta Derm Venereol 78:186-189).

As exemplified hereinbelow, the compositions of the present invention are non-irritable and highly tolerable by the skin. Furthermore, the compositions have presented a significant smoothing and tensor effect. Without wishing to be bound y any specific theory or mechanism of action, these smoothing and anti-aging effects may be attributed to the capability of the compositions to increase the skin barrier function.

Wound healing is a process that is indirectly regulated by multiple cell-adhesion molecule expression. It is known that wound healing is delayed by the absence of cell adhesion molecules. The healing of a wound may thus evidence stimulation of cell adhesion proteins. The compositions of the present invention can thus contribute to the healing of a wound in a cell monolayer culture, or the capacity of a cell to migrate across a porous membrane. Progress of wound healing can be assessed by a scratch assay. This assay is performed on either native cells or transfected cells to study the effect of specific proteins overexpression (or knockdown) on cell migration.

The in vitro scratch assay is an easy, low-cost and well-developed method to measure cell migration in vitro. The basic steps involve creating a "scratch" in a cell monolayer, capturing the images at the beginning and at regular intervals during cell migration to close the scratch, and comparing the images obtained with or without the composition of the invention to quantify the migration rate of the cells. Compared to other methods, the in vitro scratch assay is particularly suitable for studies on the effects of cell-matrix and cell-cell interactions on cell migration, mimic cell migration during wound healing in vivo and is compatible with imaging of live cells during migration to monitor intracellular events if desired. Besides monitoring migration of homogenous cell populations, this method has also been adopted to measure migration of individual cells in the leading edge of the scratch.

The impact of the extracts of the preset invention on the skin barrier function may be also evaluated ex vivo or in vitro, by any method as is known to a person skilled in the art. For example, the trans-epidermal electrical resistance (TEER) of reconstructed human skin can be measured to assess the tightness of cell layers. TEER is a direct measure of functionality of the skin barrier; it reflects all the global resistance of the tissue which is given by its own thickness as well as by its own structure. It reflects the integrality of intercellular contacts at the level of tight junctions, of the bilaminar lipidic structure that oppose penetration of outside compounds. TEER is inversely proportional to TEWL measured in vivo which is the measurement of the transepidermal water loss; the higher the TEWL, the higher the damage to the barrier function, whereas the higher the TEER, the lower the damage to the barrier function. For TEER measurement, the examined reconstructed skin is inserted into a chamber with small volume of physiological buffer (PBS), and additional volume of the buffer is applied to the top surface of the tissue. The chamber lid containing the top electrode is inserted and the resistance is measured. The TEER values (typically of treated and non-treated tissues) are determined using Millipore-ERS Volt/ohm-meter. TEER is typically presented as TEER 50, i.e. the time at which TEER is reduced by 50%.

Additional method employ quantifying the expression of filaggrin and/or desmoglein1 and/or claudin1 by a morphological analysis of in vitro skin models/reconstituted human epidermis, using immunohistochemistry staining Reconstituted human epidermis or ex vivo skin biopsies/percutaneous can be used to determine the penetration kinetics of reference molecules/dyes using, for example, Franz type diffusion cells or using Chamber systems. Reconstituted human epidermis can be also used for transglutaminase activity assay. In addition, expression profile of key genes in skin sample can also serve as an indicator of the barrier state of the skin.

Cell-cell adhesion is an important process during morphogenesis. It ensures tight contacts between neighboring cells, which are necessary for cell segregation, and for the morphological and functional differentiation of different tissues. Cell-cell adhesion plays an essential role in the homeostasis of healthy tissues, and plays a particular significant role in keeping the integrity of skin tissues.

A key structural material in the outer layer of the skin comprises a family of fibrous structural proteins named keratins. Keratin monomers assemble into bundles to form intermediate filaments, which are tough and insoluble and form strong unmineralized tissues found in reptiles, birds, amphibians, and mammals.

As exemplified hereinbelow, the present invention now shows that the extracts of the present invention enhances the expression of several key genes encoding polypeptides involved in cell to cell adhesion and in keratinocyte differentiation. Without wishing to be bound by any specific theory or mechanism of action, the maintenance and/or promotion of the skin barrier functions may be attributed to the expression of these genes.

Desmoplakin is a high molecular weight (about 332 kDa), homo-dimer protein encoded (in humans) by the DSP gene. Desmoplakin is an obligate component of functional desmosomes that anchors intermediate filaments to desmosomal plaques. The N-terminus of desmoplakin is required for its localization in the desmosome and interacts with the N-terminal region of plakophilin 1 and plakoglobin. The N-terminus is further sub divided into a region called the "Plakin domain", made up of repetitive domains called Spectrin repeats. A crystal structure of part of the plakin domain has been resolved, while the entire plakin domain has been elucidated using Small angle X-ray scattering which revealed a non-linear structure, an unexpected result considering spectrin repeats are observed in linear orientations. The C-terminus of desmoplakin binds with intermediate filaments. In the mid-region of desmoplakin, a coiled-coiled rod domain is responsible for its homodimerization. Mutations in this gene are the cause of several cardiomyopathies and keratodermas as well as the autoimmune disease paraneoplastic pemphigus. Desmoplakin has been shown to interact with Plakoglobin, Vimentin, Keratin 1 Desmin, PKP1 and PKP2.

Keratin 5, also known as type II cytoskeletal 5 keratin (K5; CK5; KRT5) and kertain 2A, also known as keratin 2E or keratin 2 are type II cytokeratins. Type II cytokeratins consist of basic or neutral proteins that are arranged in pairs of heterotypic keratin chains co-expressed during differentiation of simple and stratified epithelial tissues. The type II cytokeratin genes are clustered in a region of chromosome 12q12-q13.

In human, Keratin 5 is encoded by the KRT5 gene, and is specifically expressed in the basal layer of the epidermis with the family member KRT14 to form keratin intermediate filaments. These filaments assemble into strong networks resulting in keratinocytes attachment and anchor the epidermis to underlying layers of the skin. The network of keratin intermediate filaments provides strength and resiliency to the skin and protects it from being damaged by friction and other everyday physical stresses.

It has been suggested that keratin 5 may also play a role in transporting melanosomes, which are cellular structures that produce a pigment called melanin. The transport of these structures into keratinocytes is important for normal skin coloration (pigmentation).

Keratin 2A is encoded in humans by the KRT2A gene. It is particularly expressed in the upper spinous layer and granular suprabasal layers of normal adult epidermal tissues from most body sites.

Keratin 1 is also a member of the keratin family. It is specifically expressed in the spinous and granular layers of the epidermis with the family member keratin 10. Mutations in Keratin 1 have been associated with the variants of bullous congenital ichthyosiform erythroderma in which the palms and soles of the feet are affected. Keratin 10, also known as type I cytoskeletal Keratin 10, cytokeratin-10 (CK-10) or keratin-10 (K10) is encoded in human by the KRT10 gene. Keratin-10 is a member of the type I (acidic) cytokeratin family, which belongs to the superfamily of intermediate filament (IF) proteins.

Syndecan 1 is a protein which in humans is encoded by the SDC1 gene. The protein encoded by this gene is a transmembrane (type I) heparan sulfate proteoglycan and is a member of the syndecan proteoglycan family. The syndecans mediate cell binding, cell signaling, and cytoskeletal organization and syndecan receptors are required for internalization of the HIV-1 tat protein. The syndecan-1 protein functions as an integral membrane protein and participates in cell proliferation, cell migration and cell-matrix interactions via its receptor for extracellular matrix proteins. Altered syndecan-1 expression has been detected in several different tumor types. While several transcript variants may exist for this gene, the full-length natures of only two have been described to date. These two represent the major variants of this gene and both encode the same protein.

The cell matrix adhesion regulator (CMAR) gene has been suggested to be a signal transduction molecule influencing cell adhesion to collagen and, through this, possibly involved in tumor suppression.

Involucrin is a protein that in humans is encoded by the IVL gene. This gene is mapped to 1q21, among calpactin I light chain, trichohyalin, profillaggrin, loricrin, and calcyclin. Involucrin is a highly reactive, soluble, transglutaminase substrate protein present in keratinocytes of the epidermis and other stratified squamous epithelia. It first appears in the cell cytosol, but ultimately becomes cross-linked to membrane proteins by transglutaminase, thus helping in the formation of an insoluble envelope beneath the plasma membrane functioning as a glutamyl donor during assembly of the cornified envelope. Involucrin is synthesized in the stratum spinosum and cross linked in the stratum granulosum by the transglutaminase enzyme that makes it highly stable. It thus provides structural support to the cell, thereby allowing the cell to resist invasion by micro-organism.

Fibronectin is a high-molecular weight (~440 kDa) glycoprotein of the extracellular matrix that binds to membrane-spanning receptor proteins called integrins. In addition to integrins, fibronectin also binds extracellular matrix components such as collagen, fibrin, and heparan sulfate proteoglycans (e.g. syndecans). Fibronectin exists as a protein dimer, consisting of two nearly identical monomers linked by a pair of disulfide bonds. The fibronectin protein is produced from a single gene, but alternative splicing of its pre-mRNA leads to the creation of several isoforms. Two types of fibronectin are present in vertebrates: soluble plasma fibronectin (formerly called "cold-insoluble globulin" or CIg) is a major protein component of blood plasma (300 μg/ml) and is produced in the liver by hepatocytes; and insoluble cellular fibronectin, which is a major component of the extracellular matrix. It is secreted by various cells, primarily fibroblasts, as a soluble protein dimer and is then assembled into an insoluble matrix in a complex cell-mediated process. Fibronectin plays a major role in cell adhesion, growth, migration, and differentiation, and it is important for processes such as wound healing and embryonic development. Altered fibronectin expression, degradation, and organization have been associated with a number of pathologies, including cancer and fibrosis.

The compositions of the present invention can be formulated in any cosmetically and/or pharmaceutically, typically dermatologically suitable form as is known to a person skilled in the art. According to certain embodiments, the formulation is in the form of a lotion, gel or cream, in an ointment or oil base, as well as in a sprayable liquid form. Other suitable cosmetic product forms for the compositions of this invention include, for example, an emulsion, a mousse, a lip balm, a lip gloss, a lotion, a mask, an ointment, a pomade, a solution, a serum or a spray.

In addition to the Jojoba extract as active agent, as described herein, the compositions of the present invention can contain suitable pharmaceutically or cosmetically acceptable carriers, diluents, or excipients comprising auxiliaries which facilitate processing of the active compounds into preparations which can be used pharmaceutically or cosmetically. Further details on techniques for formulation and administration are provided in the latest edition of Remington's Pharmaceutical Sciences (Mack Publishing Co.; Easton, PA). The compositions containing the Jojoba extract of the present invention can be manufactured in a manner that is known in the art, e.g., by means of conventional mixing, dissolving, granulating, dragee-making, levigating, emulsifying, encapsulating, entrapping, or lyophilizing processes.

According to certain embodiments, the compositions of the invention further comprise one or more compatible cosmetically or pharmaceutically acceptable additives including, but not limited to fats, emulsifiers and co-emulsifiers, hydrophilic or lipophilic gelling agents, colorants, fragrances, emollients, humectants, preservatives, vitamins, chelators, thickeners, fillers, solvents, hydrophilic and lipophilic filters, dyestuffs, neutralizers, penetration enhancing agents polymers and the like, as well as other botanicals such as aloe, chamomile, and the like.

According to certain embodiments, the additive is selected from the group consisting of ascorbic acid, its derivatives and corresponding salts, glycerin, citric acid, acetic acid, sulfites, phenoxyethanol, EDTA, diethylmalate, t-Butyl-hydroquinone, aminoguanidine, nicotinic acid/Niacin, nicotinamide, stannous chloride, glucose oxidase, polyvinylpolypyrrolidone, phosphoric acid and cosmetically/pharmaceutically acceptable base. Each possibility represents a separate embodiment of the present invention.

According to certain typical embodiments, the compositions are applied topically.

One skilled in the art is capable of determining the effective dose or amount of the compositions comprising the Jojoba extract as well as of the application regime. The effective dose and regime refers to that required to maintain or promote the skin barrier functions of the skin, as may be measured, for example, by measuring the TEWL or any other method as described herein and as in known to a person skilled in the art.

According to certain embodiments, the compositions of the present invention comprise the Jojoba extract at a concentration of from 0.003% to 30%, weight to weight (w/w) in respect to the total weight of the composition. According to some embodiments, the Jojoba extract is in the range of 0.3% to 10%. According to typical embodiments, the concentration of the Jojoba extract within the composition is from 1% to 3% (w/w) in respect to the total weight of the composition.

The exact dose will be determined by the practitioner according to certain factors related to the individual requiring treatment, including the severity of the individual's particular state, general health of the individual, age, weight, and gender of the individual, diet, time and frequency of administration, drug combination(s), reaction sensitivities, and tolerance/response to treatment. As a general guide, long-acting cosmetic compositions can be administered once daily, every 2 to 4 days, every week, or once every two weeks, depending on half-life and clearance rate of the particular formulation. Variations in these dosage levels can be adjusted using standard empirical routines for optimization, as is well known to a person skilled in the art. Guidance as to particular dosages and methods of delivery is provided in the literature and is generally available to practitioners in the art.

According to yet additional aspect, the present invention provide a composition effective maintaining and/or promoting the skin structure, strength, cohesion or any combination thereof thereby maintaining or promoting said skin barrier functions comprising a Jojoba extract, the extract produced by the steps of:

(a) mixing a Jojoba plant or any part thereof with at least one polar solvent;

(b) incubating the mixture for a time period sufficient to form a liquid extract;

(c) removing the Jojoba plant or parts thereof and collecting the liquid extract;

(d) filtering the liquid; and (e) collecting the filtrate.

According to certain embodiments, incubating the mixture comprises incubation for a period of from 10 min to 24 h, typically from 40 min to 12 h, more typically from 40 min to 2 h. According to additional embodiments, the incubation temperature is in the range of 20-120° C., typically of 60-120° C., more typically 80-110° C.

According to certain embodiments, step (c) comprises centrifugation for removing the Jojoba plant parts. According to other embodiment, step (d) comprises filtering the liquid extract through a sieve. According to yet additional embodiments, the method further comprises filtering the filtrate of step (e) through a filter having a pore size of less than 1.5μ.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1

Manufacturing the Jojoba Extract

Vivid and non-contaminated Jojoba plants have dark green to brown color. Accordingly, plant parts taken for extraction were examined for their color. Yellow bright leaves or plant parts showing spots, particularly white spots, were removed. The plant parts were then partially or completely dried. Dry plant parts were added to water at 1:2 to 1:5 ratio, typically at a 1:2 ratio (plant parts:water) at room temperature. The mixture was heated for duration of 2 hours at 100° C. and left to cool over night. Solids were removed by centrifugation at 4500 rpm for 30 min (Sigma Laborzentrifugen 3-10 3645 g). The supernatant was collected and filtered through 1.2 micron filter, then through 0.45 micron filter and lastly though 0.22 micron filter and the filtrate was collected. To the filtrate, 1% ascorbic acid 1% and 50% Glycerin were added to form the final composition.

Composition specifications were as follows: Dry Weight: 36-41 mg/g; pH—4-4.3, Trolox Equivalent (TAA) 120 mM. Polyphenols values: 22200 mg/L; Gallic acid equivalent (GAE), clear solution, brown colored.

Example 2

Effects of Jojoba Extract on Keratinocytes Gene Expression Profile cDNA array gene expression study was performed with Jojoba extract at 0.03% (hBA15m-NHEK batch 15/10/07, prepared as described in Example 1 hereinabove at a leaves:water ratio of 1:2; phenol content 7617.7 mg/L Gallic acid equivalent; Trolox equivalent 108.6 mM; with no added preservatives). Dilutions of the source extract were done with the assay medium (see below).
Materials and Methods
Biological Model
Cellular type: Normal human epidermal keratinocytes (NHEK) $K_{074}$ used at the $3^{rd}$ passage
Culture Conditions 37° C., 5% $CO_2$
Culture medium: Keratinocyte-SFM (Invitrogen 17005-034) supplemented with Epidermal Growth Factor (EGF) 0.25 ng/ml-Pituitary extract (PE) 25 µg/ml (Invitrogen 3700015) Gentamycine 25 µg/ml (Sigma G1397)
Assay medium: Keratinocyte-SFM (Invitrogen 17005-034) supplemented with Gentamycine 25 µg/ml (Sigma G1397)
Preliminary Cytotoxicity Assay
 plate format: 96-well
 cells/well: 20000 NHEK, Keratinocyte-SFM -EGF -PE medium
 replicates: 6
 concentration range: see Table 2
 cells/compound contact: 24 hours
 evaluation parameter: MTT reduction assay and morphological observations with microscope (objective ×10)
Culture and Treatment Normal human epidermal keratinocytes (NHEK) cells were seeded in 12 wells plates in culture medium until confluence, and then placed in the assay medium. The Jojoba extract was then added to the test wells and cells were cultivated for 24 hours at 37° C. and 5% $CO_2$. Cells cultivated in assay medium alone were used as a control. Each condition (test/control) was performed in n=3.

At the end of the incubation time, the cells were washed in PBS solution (Invitrogen 14190094); 300 µl of TriReagent were added and the cells were immediately frozen at −80° C.
Analysis of Differential Expression by Mini-chips The analysis of gene expression was performed using standard mini-chips dedicated to the study of gene expression and specially adapted to the screening purposes (produced by BIOalternatives, France).

These Nylon chips (<3 cm$^2$) were spotted using BIOalternatives spotting device (non-contact spotter, piezo technology, Piezorray, PerkinElmer) and cDNAs specific markers of interest. The analysis was made using a proprietary technology allowing the miniaturization of the currently used formats and cost-effective analysis. It was based on the use of mRNA as a template for reverse transcription and $^{33}$P label (optimal sensitivity). A summary description of the examined genes in this experiment is presented in Table 1 hereinbelow.

Figure 2A:
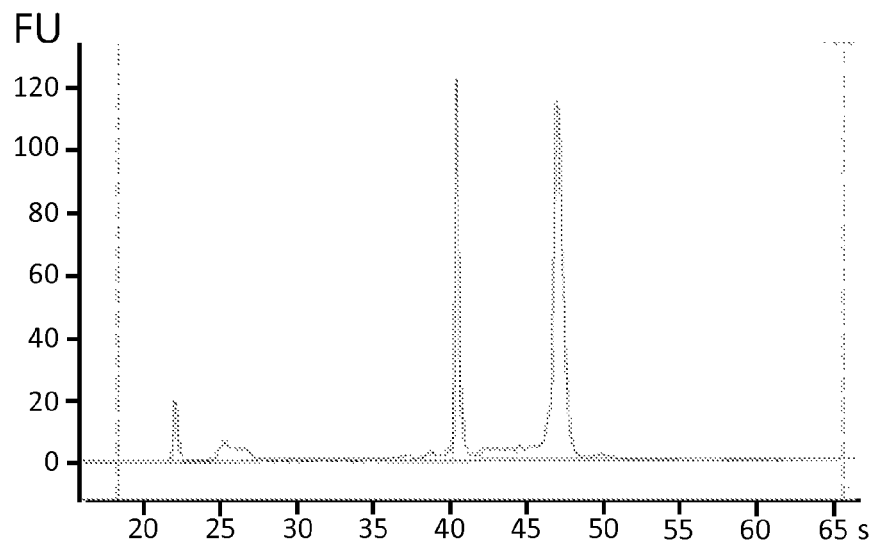
FIG. 2A: Control: RNA concentration: 2.45 μg/μl; RNA quantity: 36.75 μg.
Figure 2B:
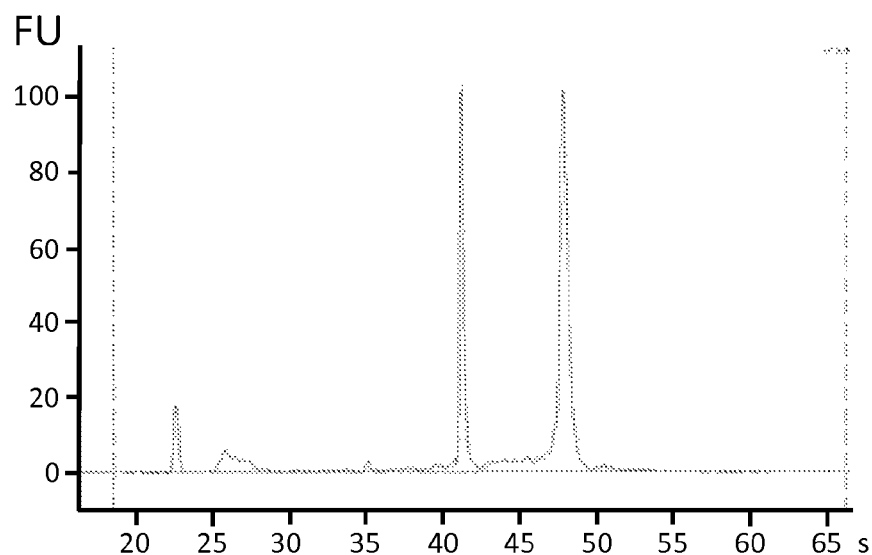
FIG. 2B: Culture treated with 0.03% Jojoba extract: RNA concentration: 1.97 μg/μl; RNA quantity: 29.55 μg.

The mRNA of each culture was extracted using TriReagent (standard protocol). The multiple cDNA $^{33}$P-labelled targets were prepared by direct reverse-transcription of mRNA, using [$^{33}$P]-dATP and oligodT. The RNA quality controls are presented in FIG. 2.

These labeled cDNA targets were hybridized to the specific cDNA probes covalently fixed to the mini-chips. After extensive washing, the relative amount of each specific target hybridized to its probe was revealed by PhosphorImaging.

The analysis was performed by direct quantification of spot radioactivity using a "Cyclone" PhosphorImager (Packard instruments; 72 h exposition) and ImageQuant TL, an image analysis Software (Amersham Biosciences).

TABLE 1

Structure of the support mini-chip containing 164 genes (+control and housekeeping genes) for evaluating the effect of the Jojoba extract

|   | 1 | 2 | 3 | 4 | 5 | 6 | 7 | 8 | 9 |
|---|---|---|---|---|---|---|---|---|---|
| a |   | A |   | B |   | C |   | D |   |
| b | E | LGALS7 | ACAS2 | ADFP | AZGP1 | KI67 | AQP3 | AQP8 | B2M |
| c | BPAG1 | CDH1 | CD14 | KAI1 | CALML5 | CAMP | CAPNS1 | CASP14 | CTNNA1 |
| d | CTNNB1 | CAV1 | CMAR | CDSN | CLDN1 | CRNN | CST6 | CSTA | KRT1 |
| e | KRT5 | KRT6A | KRT10 | KRT14 | KRT16 | BLANC | KRT19 | KRT2E | DSC1 |
| f | DSC3 | DSG1 | DSP | EVPL | FABP5 | FLG | EPPK1 | FAS | FTH1 |
| g | G6PD | GBA | HMGCR | UGCG | ID1 | ITGA2 | IVL | KIT | KLF4 |
| h | KLK5 | KLK6 | KLK7 | LOR | NICE-1 | OCM | ODC1 | PADI1 | PADI2 |
| i | PADI3 | PXN | CRABP2 | LAMR1 | RPTN | S100A7 | S100A8 | S100A9 | S100A12 |
| j | SPTLC1 | SPTLC2 | SPRL1B, XP5 | SPRR1A | SPRR1B | SPRR2A | LCE3D, SPRL6A, LEP16 | SRD5A1 | SFN |

TABLE 1-continued

Structure of the support mini-chip containing 164 genes (+control and housekeeping genes) for evaluating the effect of the Jojoba extract

|   | 1 | 2 | 3 | 4 | 5 | 6 | 7 | 8 | 9 |
|---|---|---|---|---|---|---|---|---|---|
| k | SULT2B1 | SAS | SBS | BLANC | TGM1 | THH | ZYX | CD44 | COL16A1 |
| l | COL4A1 | COL4A2 | COL7A1 | COL17A1 | DEFB4 | PI3 | FN1 | HAS3 | HYAL2 |
| m | HYAL4 | LAMB2 | LAMC2 | LOXL2 | MATN2 | MMP1 | MMP11 | MMP14 | MMP2 |
| n | MMP3 | MMP9 | MMP19 | MME | SERPINE1 | SERPINB2 | PLAT | PLAU | SPARC |
| o | SYND1 | TIMP1 | CALM3 | EDN1 | EGF | EGFR | GMCSF | HBEGF | FGF2 |
| p | IGF1 | IGF1R | IL1A | IL1B | IL1RA | IL1R1 | IL1R2 | IL11 | IL8 |
| q | PLAB | CXCL5 | PDGFA | TLR1 | TLR4 | TGFB1 | TRPV3 | TNF | VEGFA |
| r | CAT | CD59 | GPX1 | GSR | HMOX1 | HSP27 | HSPA1A | HSPCA | MT1H |
| s | SOD1 | SOD2 | TXN | MIF | RNASE7 | SCEL | SLC6A6 | SMPD1 | SPINK5 |

Quantitative RT-PCR
Reverse Transcription
  Total RNA was extracted from each sample using Tri-reagent according supplier advices.
  Potential contaminant traces of DNA were removed using the DNAfree system (Ambion ref 1906).
  The reverse-transcription of mRNA was conducted in the presence of oligo(dT) and Superscript II reverse-transcriptase (Invitrogen).
Real-time PCR Analysis
  The PCR reactions were performed in triplicate using the LightCycler® system (Roche Molecular Systems Inc.) in accordance with the protocol recommended by the supplier. This system allows rapid and powerful PCR reactions, after determining the analysis conditions of the tested primers. It consists of two components:
  A thermo-cycler: optimized for rapid PCR applications; allowing extremely rapid thermal transfers within the reaction mixture.
  A fluorimeter: allowing constant fluorescence measurement of the intercalating dye SYBR Green I; dye that specifically binds to double-stranded DNA during the elongation cycle (detection wavelength: 521 nm).
  The real time (RT) PCR was used for quantitative analysis of candidate genes showing elevated expression in the above-described mini-chip assay. 23 kDa highly basic protein, also designated the 60S ribosomal protein L13A (RPL13A, accession No. NM_002423) was used as an internal standard control, the amplification of which resulted in a fragment of 483 bp. Three genes were examined: Cytokeratin 5, Desmoplakin and Sirtuin 1.
Quantitative PCR Data Management
  The incorporation of the fluorescent dye into the amplified DNA was measured continuously during the PCR cycles. The results were drawn as "fluorescence intensity" versus "PCR cycle" plot, allowing the evaluation of a relative expression (RE) value for each marker.
  The value selected for RE calculations is the "output point" of the fluorescence curve. For a considered marker, the highest is the cycle number and the lowest is the mRNA quantity
  The RE value was expressed in arbitrary units (AU) according to the formula:

$$(1/2^{number\ of\ cycles}) \times 10^6$$

Data Management
  The raw data were analyzed with Microsoft Excel® software.
  Standard error of the mean (sem) was calculated as mean=Sd/√n
  Percentage of viability (%) was measured as (OD sample/OD control)×100
Results
Cytotoxicity Preliminary Assay
  Table 2 summarizes the effect of the Jojoba extract on the viability of keratinocyte cultures.

TABLE 2

Effect of Jojoba extract on the viability of keratinocyte

|  | Control | Jojoba Extract (%) | | | | | | | |
|---|---|---|---|---|---|---|---|---|---|
|  |  | 0.0046 | 0.0137 | 0.041 | 0.123 | 0.370 | 1.111 | 3.333 | 10.0 |
| Viability (%) | 108  109 | 92 | 93 | 91 | 82 | 79 | 49 | 33 | 53 |
|  | 93   97 | 80 | 86 | 76 | 74 | 65 | 40 | 30 | 47 |
|  | 92  104 | 84 | 77 | 80 | 74 | 72 | 39 | 29 | 52 |
|  | 96  103 | 85 | 83 | 73 | 74 | 68 | 39 | 30 | 46 |
|  | 96  102 | 84 | 77 | 86 | 82 | 77 | 49 | 31 | 45 |
|  | 97  102 | 82 | 86 | 83 | 73 | 77 | 45 | 31 | 48 |
| Average | 100 | 85 | 84 | 81 | 76 | 73 | 43 | 31 | 49 |
| Sem | 2 | 2 | 2 | 3 | 2 | 2 | 2 | 1 | 1 |
| Morphological observations | + | + | + | +, g | ±, g | (−), g | (*), g | op | op |

+: normal population;
+/−: growth reduction;
(−): toxicity;
0: cell mortality;
g: grains of compounds;
*morphological modification;
ag: agglutinated cells;
Sem: standard error of the mean Analysis of Gene Expression by Mini-chips The mini-chip design with all tested genes is presented in Table 1 hereinabove. FIG. 1 shows expression of the tested genes in control keratinocytes (FIG. 1A) compared to keratinocytes treated with 0.03% Jojoba extract for 24 h (FIG. 1B).

Analysis of Gene Expression by Quantitative RT-PCR

The following classification of gene expression was used:

| Relative expression (% of control) | Classification of the effects |
|---|---|
| >150% and <200% | Moderate stimulation, to be confirmed |
| >200% | Stimulation |
| >300% | Strong stimulation |
| <65% and >50% | Moderate inhibition |
| <50% and >30% | Inhibition |
| <30% | Strong inhibition |

The following genes were shown to be stimulated:

Cytokeratin 5 (K5; CK5), also designated type II cytoskeletal 5 keratin (KRT5); 58-kDa cytokeratin: 229% relative expression (=stimulation);

Desmoplakin I & II (DSP; DPI & DPII): 185% relative expression (=moderate stimulation);

Cytokeratin 2E/A (K2E; CK2E), also designated type II cytoskeletal 2 epidermal keratin (KRT2E; KRT2A); (epidermal ichthyosis bullosa of Siemens): 160% relative expression (=moderate stimulation);

Cytokeratin 1 (K1; CK1), also designated type II cytoskeletal 11 keratin (KRT11); 67-kDa cytokeratin; hair alpha protein: 156% relative expression (=moderate stimulation);

Syndecan-1 (SYND1; SDC1), also designated CD138 antigen: 160% relative expression (=moderate stimulation);

Cell matrix adhesion regulator (CMAR; CAR): 146% relative expression (=moderate stimulation);

Cytokeratin 10 (K10) also designated type I cytoskeletal 10 keratin: 146% relative expression (=moderate stimulation);

Involucrin: 154% relative expression (=moderate stimulation);

Fibronectin (FN): 146% relative expression (=moderate stimulation);

Example 3

Toxicity Assessment of the Jojoba Extract

Skin tolerance to the Jojoba extract was measured by single application of the extract to the back skin of healthy adult volunteers, under occluded patch for 48 h.

Twenty four volunteers at age 18-70, female or male, free from dermatological lesions on the area studied and being able to fulfill the study verbal requirements participated in the study. The Jojoba extract produced as described in Example 1 herein above (leaves:water ratio of 1:2, phenol content 13,110 mg/L Gallic acid equivalent; Trolox equivalent 92.5 mM) was diluted ×2. 0.02 ml was applied to the skin of the back of each volunteer, under a patch. Examination of the contact zone was carried out just before the study in order to apply the product to a surface free from macroscopic irritation marks, scars or any abnormalities which could interfere with reading of the results. An empty patch was applied in parallel as a negative control.

After 48 h, the patches were removed, and the area was assessed by a dermatologist for erythema; dryness/desquamation; oedema and vesicles according to a predetermined scale.

Under the above experiment conditions, after a single application of 0.02 ml of Jojoba extract diluted at 50%, under occluded patch during 48 h, on 24 healthy volunteers, the extract was defined as non-irritant regarding its primary skin tolerance.

Example 4

Trans-Epidermal Water Loss (TEWL) Measurement

The Trans Epidermal Water Loss (TEWL) was examined in a double-blind assay with eleven healthy female volunteers (43 to 67 years of age). TEWL was measured on the forearms of the volunteers before the first application (D0) and after 28 days of application (D28) using Tewameter® (Courage & Khazaka). Two measurements were taken on each forearm, and the average was calculated. The TEWL variation, in percentage, was calculated between D0 and D28. A decrease of the TEWL represents improvement of the skin barrier function.

Each volunteer used the assay product (a gel containing 5% of Jojoba extract, the specification of which appear in Table 3 hereinbelow) and a placebo (same gel without Jojoba extract, substituted with glycerin and water). Each product was applied to a different forearm, in a randomized pattern.

TABLE 3

Composition of the assay product

| Substance | % |
|---|---|
| Water | 76.10 |
| Caprylic/Capric Triglycerides | 6.00 |
| Cetearyl Alcohol | 3.50 |
| Glyceryl Stearate and PEG-100 Stearate | 1.50 |
| Cetearyl Alcohol and Ceteareth-20 (Sabowax FL 10) | 1.50 |
| Polysorbate 60 | 2.00 |
| Glyceryl MonoStearate SE | 0.60 |
| Stearic Acid | 2.50 |
| Phenonip ® (Phenoxyethanol, Methyl paraben, Ethyl paraben, n-Butyl paraben, Butyl paraben, Propyl paraben and Isobutyl paraben ) | 0.90 |
| Xanthan gum | 0.30 |
| Edetate Disodium | 0.10 |
| glycerin 50%, water, *Simmondsia chinensis* (Jojoba) Leaf Extract; Ascorbic acid 1%. | 5.0 |

The assay and placebo products were applied by the volunteers themselves to the designated area every day, twice a day (on the morning and on the evening) during 28 days of the trial. The area was cleaned before application; the products were massaged until complete product penetration; quantity was as necessary.

The average of the two TEWL measurements taken was kept as the experimental value. TEWL variation between D0 and D28 is presented (in %) in Table 4:

TABLE 4

TEWL variation (%) for the two products

| Volunteer No. | Assay Product | Placebo |
|---|---|---|
| 1 | −9% | 15% |
| 2 | 5% | 6% |
| 2 | −27% | −20% |
| 4 | −11% | −20% |
| 6 | −24% | −27% |
| 7 | −1% | 12% |
| 8 | −24% | −33% |
| 9 | 9% | 47% |
| 10 | −5% | 6% |
| 11 | −4% | −23% |
| 12 | −38% | −32% |
| Average | −12% | −6% |
| Std | 15% | 25% |
| Maximum | 9% | 47% |
| Minimum | −38% | −33% |
| Student t test | 2% | 16% |

The assay product with 5% Jojoba extract applied twice a day for 28 days by 11 female volunteers showed a statistically significant improvement of the skin barrier function with 12% decrease of the TEWL, while the TEWL variations for the placebo gel were not significant.

Example 5

Effect of Jojoba Extract on Skin Cohesion and Appearance

The anti-aging effect of Jojoba extract was assessed by examining the cutaneous relief parameters in vivo using Dermatop® (EOTECH—France). The cutaneous relief parameters included the average roughness (Ra); maximum amplitude (Rt); and average relief (Rz).

The assay is based on calculating a phase image from images with interference fringe projection. This image then allows determining the height of each point. The acquisition software allows to obtain 2D and 3D measurements and to determine parameters of the cutaneous relief on 50 vertical profiles distributed along the zone of interest. An automatic system of repositioning allows the precise re-identification of the zone of measurement.

Twenty six (26) healthy female volunteers (46-64 years of age) participated in this study. Application regime was as described in Example 4 hereinabove. The assay product was a gel containing 3% of Jojoba extract (designated IBRGapture®, the specification of which appear in Table 5 hereinbelow) and a placebo (same gel without Jojoba extract, replaced with water, glycerin and sodium metabisulfite in proportions corresponding to the levels contributed by the extract in the active gel, and with the addition of appropriate FD&C colorants to match the active product's final color).

TABLE 5

Composition of the assay product IBRGapture ®

| INCI/chemical name | Tradename | % |
|---|---|---|
| Water | Water | 81.34 |
| Butylene glycol | 1,3-butanediol | 4.00 |
| Dipropylene glycol | Dipropylene glycol | 1.00 |
| Hexylene glycol | Hexylene glycol | 1.00 |
| Glycerin | Glycerin | 2.00 |
| Polysorbate 20 | Tween 20 | 1.00 |
| Cyclomethicone | SF0005Z | 4.00 |
| C12-15 Alkyl Benzoate | Saboderm AB | 0.50 |
| Isononyl isononanoate | SabodermISN | 0.50 |
| Cetearyl Octanoate | SabodermCSO | 0.50 |
| Decyl oleate | Decil oleate | 0.50 |
| Glycerin, water, and *Simmondsia chinensis* (Jojoba) Leaf Extract | IBRGapture ® 1101 | 3.00 |
| Carbomer | Carbopol 940 | 0.80 |
| Triethanolamine | Triethanolamine | 0.70 |
| Phenoxyethanol | Phenoxyethanol | 0.40 |
| Methyl paraben | Nipagin M | 0.15 |
| EDTA | EDTA | 0.10 |
| Sodium metabisulfite | Sodium metabisulfite | 0.0060 |
| FD&C red 4 | Allura red | 0.00024 |
| FD&C yellow 5 | Tartrazine | 0.00014 |
| FD&C blue 1 | Erioglaucine | 0.00002 |

The studied parameters were:
(1) Ra: the average roughness (in μm): a decrease in this parameter characterizes a smoothing effect; (2) Rz: the average relief (in μm): average of all picks-to-valley heights; (3) Rt: the relief amplitude (in μm): average of the 5 maximum picks-to-valley height.

A decrease in one of these parameters (Rt and Rz) characterizes a tensor effect of the product.

Figure 3:
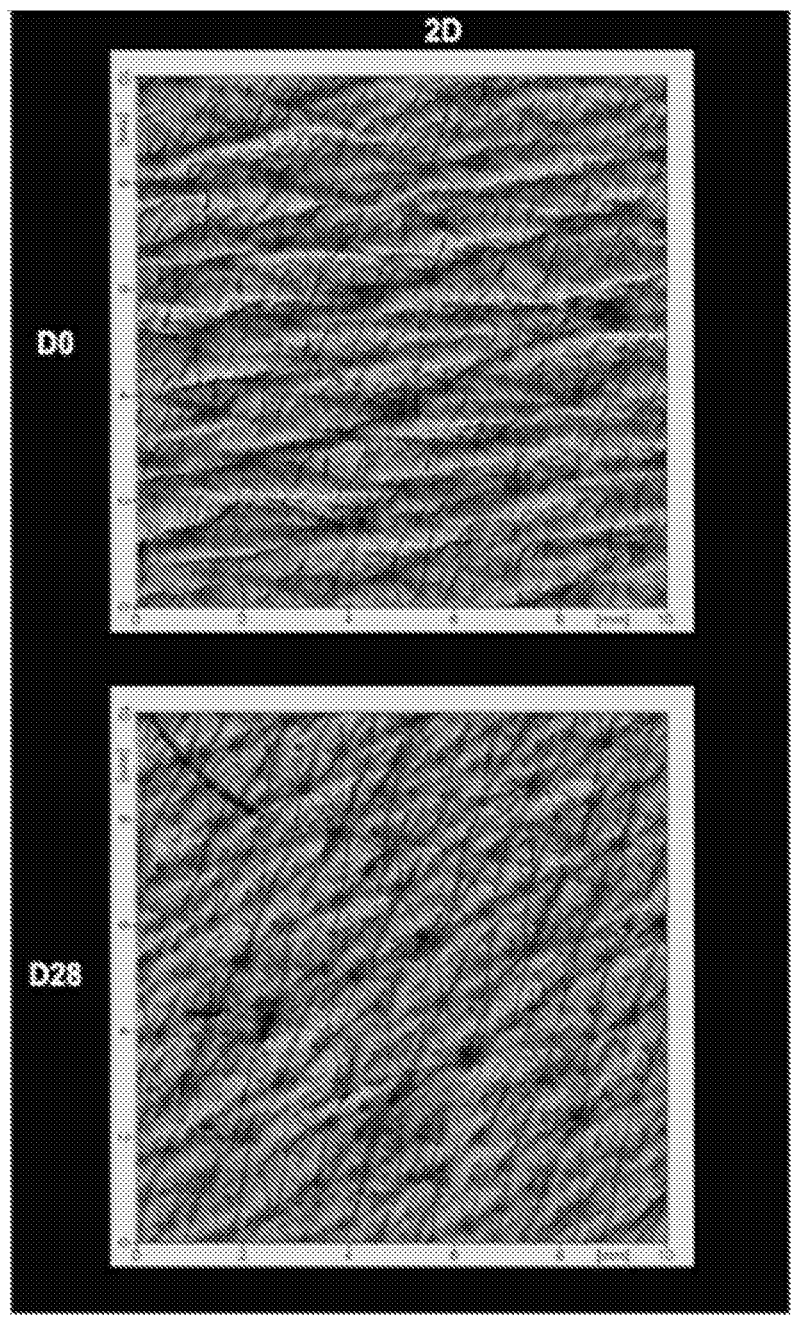
FIG. 3 demonstrates the visual effect of a composition comprising 3% jojoba extract on the skin relief

All parameters were measured before ((D0) and after (D28) the products application. A synthesis of the results is presented in Table 6 hereinbelow. The visual effect on the skin is presented in FIG. 3.

TABLE 6

Variation of the cutaneous relied parameters

| | | Δ (mean ± SEM) | Δ% on mean | Student t test P | Significant | % of subjects with the expected effect |
|---|---|---|---|---|---|---|
| Assay Product | Ra (in μm) | −2.1 ± 0.8 | −6% | 0.019 | Yes | 65% |
| | Rz (in μm) | −8.6 ± 3.4 | −8% | 0.016 | Yes | 65% |
| | Rt (in μm) | −18.0 ± 7.6 | −9% | 0.026 | Yes | 73% |
| Placebo | Ra (in μm) | −1.3 ± 1.0 | −4% | 0.215 | No | 54% |
| | Rz (in μm) | −6.4 ± 3.3 | −5% | 0.065 | Limit | 65% |
| | Rt (in μm) | −13.0 ± 6.6 | −6% | 0.061 | Limit | 69% |

Under these study conditions, after 28 days of use, the assay product containing the Jojoba extract induced:
- A significant decrease in the average roughness (Ra) of −2.1 μm on average, that is −6%;
- A smoothing effect observed in 65% of subjects;
- A significant decrease in the average relief (Rz) of −8.6 μm on average, that is −8%.
- A significant decrease in the relief amplitude (Rt) of −18.0 μm on average, that is −9%; and
- A tensor effect observed in 65% to 73% of subjects.

In summary—a significant decrease in the average roughness is observed, indicating a significant smoothing effect of the active product. A significant decrease in the average relief and a significant decrease in the relief amplitude are found resulting in significant tensor effect of the active product.

Example 6

Effect of Jojoba Extract on Cellular Cohesion

The effect of Jojoba extract (IBRGapture® described in Example 5 hereinabove) on the stratum corneum cohesion is evaluated by analysis of skin samples removed with D-Squam® from forearms. The pressure exerted during the application of D-Squam® is controlled using QDerm®.

The sample analysis is performed using Skin Image Analyser® (S.I.A®) with QuantiSquam® software: the surface of stripping is lightened in a standardized way (35°) and observed with a digital camera linked to a computer. The area studied is of 1 cm$^2$.

The digitized image obtained is analyzed in grey levels in order to determine the surface occupied by the removed squamae (in mm$^2$) and the desquamation index (ratio between the occupied surface and the thickness of the cellular layers).

Very close zones are defined on forearms. A first sample is taken with DSquam® on the first zone (t0) to define the basal quantity of squamae. Other samples are taken immediately after application of the assay product IBRGapture® (t1) and at various kinetics (ti).

The difference between t1 and t0 gives information about the quantity of squamae removed by the product application.

The difference between (ti–t0) and (t1–t0) gives information about the stratus corneum cohesion due to the assay product: if less squamae are sampled 2 hours after application than immediately after application, it means that the product increased the cohesion between corneocyte which therefore remained on the skin.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for maintaining and/or promoting skin structure, strength, cohesion or any combination thereof comprising administering to the skin of a subject in need thereof a composition comprising as an active ingredient a polar solvent extract of raw Jojoba (*Simmondsia chinensis*) plant or part thereof,
   wherein the extract is produced by a method comprising the steps of:
   a. mixing a raw Jojoba plant or any part thereof with at least one polar solvent;
   b. incubating the mixture for a time period sufficient to form a liquid extract wherein the incubation temperature is in the range of 20° C.-120° C.;
   c. removing the Jojoba plant or parts thereof and collecting the liquid extract;
   d. filtering the liquid extract; and
   e. collecting the filtrate;
   wherein the extract is effective in promoting cell to cell adhesion in said skin;
   thereby promoting cell to cell adhesion and maintaining and/or promoting the skin structure, strength, cohesion or any combination thereof and maintaining or promoting the skin barrier function.

2. The method of claim 1, wherein maintaining or promoting the skin barrier function comprises at least one of maintaining or reducing the skin dehydration rate; maintaining or promoting the skin hydration value; maintaining or promoting protection from environmental hazards and any combination thereof.

3. The method of claim 1, wherein said method is effective in at least one of maintaining or improving the skin health, skin integrity, skin firmness, skin extensibility, skin elasticity, overall skin appearance and any combination thereof.

4. The method of claim 3, wherein improving the skin health comprises at least one of relieving the symptoms of eczema, dermatoses, psoriasis vulgaris, lichen planus, ichthyosis, ichthyosis vulgaris and cholangitis; preventing blistering disorders; maintaining normal skin homeostasis; facilitating skin wound healing and any combination thereof.

5. The method of claim 3, wherein promoting the overall skin appearance comprises at least one of preventing the visible signs of aging and weathered skin including wrinkles and lines; evening of skin surface; reducing skin pore size or any combination thereof.

6. The method of claim 1, wherein said method further comprises determining the maintenance and/or promotion of the skin structure, strength, cohesion or barrier function in comparison to a predetermined threshold value.

7. The method of claim 6, wherein the predetermined threshold is a value measured before administering the composition to the skin.

8. The method of claim 6, wherein the predetermined threshold is an average value obtained from individuals with healthy skin.

9. The method of claim 6, wherein the predetermined threshold is an average value obtained from individuals with disturbed skin.

10. The method of claim 1, wherein the polar solvent is selected from the group consisting of water, ethanol, propylene glycol, butylene glycol, methanol, glycerol, propanol, butanol, dipropylene glycol, pentylene glycol, hexylene glycol, dimethyl formamide, acetonitrile, dimethyl sulfoxide, dichloromethane, ethyl acetate, tetrahydrofuran, formic acid, acetic acid, acetone and any combination thereof.

11. The method of claim 10, wherein the polar solvent is water.

12. The method of claim 10, wherein the polar solvent is water and at least one of ethanol, propylene glycol, butylene glycol, methanol, glycerol and acetone.

13. The method of claim 1, wherein the composition is a cosmetic or pharmaceutical composition further comprising a cosmetically or pharmaceutically acceptable diluent, carrier or excipient.

14. The method of claim 13, wherein the cosmetic or pharmaceutical composition is formulated for topical application.

15. The method of claim 1, wherein the composition further comprises at least one additional active ingredient.

16. The method of claim 1, wherein the filtrate of step (e) is further filtrated through a filter having a pore size of less than 1.5μ.

17. The method of claim 1, wherein the Jojoba plant part is selected from the group consisting of roots, stems, leaves, seeds, fruit or any combination thereof.

18. The method of claim 1, wherein the Jojoba plant or part thereof is in a form selected from the group consisting of fresh, partially dried or completely dried.

19. The method of claim 1, wherein the maintaining and/or promoting the skin structure, strength, cohesion or any combination thereof comprises activating at least one gene encoding a polypeptide involved in cell to cell adhesion and/or in keratinocyte differentiation.

20. The method of claim 19, wherein the polypeptide involved in cell to cell adhesion is selected from the group consisting of desmoplakin I, desmoplakin II, syndecan 1, involucrin and fibronectin.

21. The method of claim 19, wherein the polypeptide involved in keratinocyte differentiation is selected from the group consisting of cytokeratin 5, cytokeratin 2E/A, cytokeratin 1 and cytokeratin 10.

\* \* \* \* \*